United States Patent

Thomas et al.

[11] Patent Number: 5,549,629
[45] Date of Patent: Aug. 27, 1996

[54] APPARATUS FOR COVERING A SURGICAL NEEDLE TO PROTECT THE USER

[76] Inventors: Stacy I. Thomas; Rose Akerman, both of 417 N. Walnut St., Milford, Del. 19963

[21] Appl. No.: 208,479

[22] Filed: Mar. 10, 1994

[51] Int. Cl.$^6$ .................................................. A61B 17/00
[52] U.S. Cl. ................................. 606/223; 606/222; 163/5
[58] Field of Search ................................ 606/222–227, 606/139, 144, 147, 148, 151, 205, 207; 223/102, 104; 163/5; 289/16

[56] References Cited

U.S. PATENT DOCUMENTS 5,180,385  1/1993  Sontag ..................................... 606/223

FOREIGN PATENT DOCUMENTS 766552  6/1934  France ................................... 606/147
WO93/13714  7/1993  WIPO .................................... 606/148

Primary Examiner—Stephen C. Pellegrino
Assistant Examiner—Jeffrey A. Schmidt
Attorney, Agent, or Firm—Walter G. Finch

[57] ABSTRACT

This invention provides for a novel retractable, telescoping, surgical needle cover and a collapsible needle, such that the sharp tip of the needle is covered after use thereby protecting the user from accidental needle sticks. In one embodiment, the needle cover is hollow and holds the needle at the tip. When the sharp tip is struck on a hard surface, the needle collapses inside of the needle cover. A second embodiment of the invention provides for a cover which slides back and forth along the length of a needle and is held in a forward position by a lever which is movably disposed within a groove at the base of the needle. In the third embodiment, the needle cover only partially the covers the outer surface of the needle, and when the needle is held by a needle holder such that the needle holder contacts both the cover and the needle, then the needle tip is exposed. When the needle is gripped by the needle holder such that only the needle cover is held, the tip of the needle is struck on a hard surface and the needle cover slides forward to cover the tip.

1 Claim, 4 Drawing Sheets

APPARATUS FOR COVERING A SURGICAL NEEDLE TO PROTECT THE USER

BACKGROUND AND SUMMARY OF THE INVENTION

This invention relates to surgical needles, and more particularly to covers for the sharp tips of surgical needles. The invention provides for a retractable, collapsible cover and a telescoping needle, such that after the sharp tip of the needle has pierced the flesh of a patient during surgery and become contaminated, the medical person handling the needle will be protected from an accidental needle-stick of the sharp tip and thereby be protected from the transmission of blood borne viruses such as hepatitis and AIDS. The cover will slide forward for protection covering the sharp tip and backward for use in surgery exposing ther sharp tip.

It is an object of this invention to provide a novel cover for a surgical needle.

It is another object of this invention to provide an embodiment in which the needle is slidably positioned inside a hollow needle cover at the furthermost tip of the cover so that the sharp point of the needle extends through an opening at the tip of the needle cover and the needle collapses inside the needle cover when the sharp point of the needle is struck on a hard object, but does not collapse when piercing the soft flesh of a patient during surgery.

It is a further object of this invention to provide an embodiment wherein the needle is positioned inside a hollow needle cover, such that the needle cover slides forward and backward over the sharp tip of the needle, and the needle cover is held in a forward position by a lever mechanism movably disposed within a groove on the base of the needle.

It is still another object of this invention to provide an embodiment wherein a needle is slidably disposed within a hollow needle cover, such that the needle cover does not slide forward while the needle is gripped by a needle holder, but when the needle holder is positioned so that it is gripping the needle cover only, the needle cover will slide forward to cover the sharp point of the needle when the sharp tip is struck on a hard object, but not when the needle pierces the soft flesh of a patient during surgery.

These and other objects and attendant advantages of this invention will become more obvious and apparent from the following detailed specification and accompanying drawings.

DESCRIPTION OF THE PREFERRED EMBODIMENTS OF THE INVENTION

Figure 1:
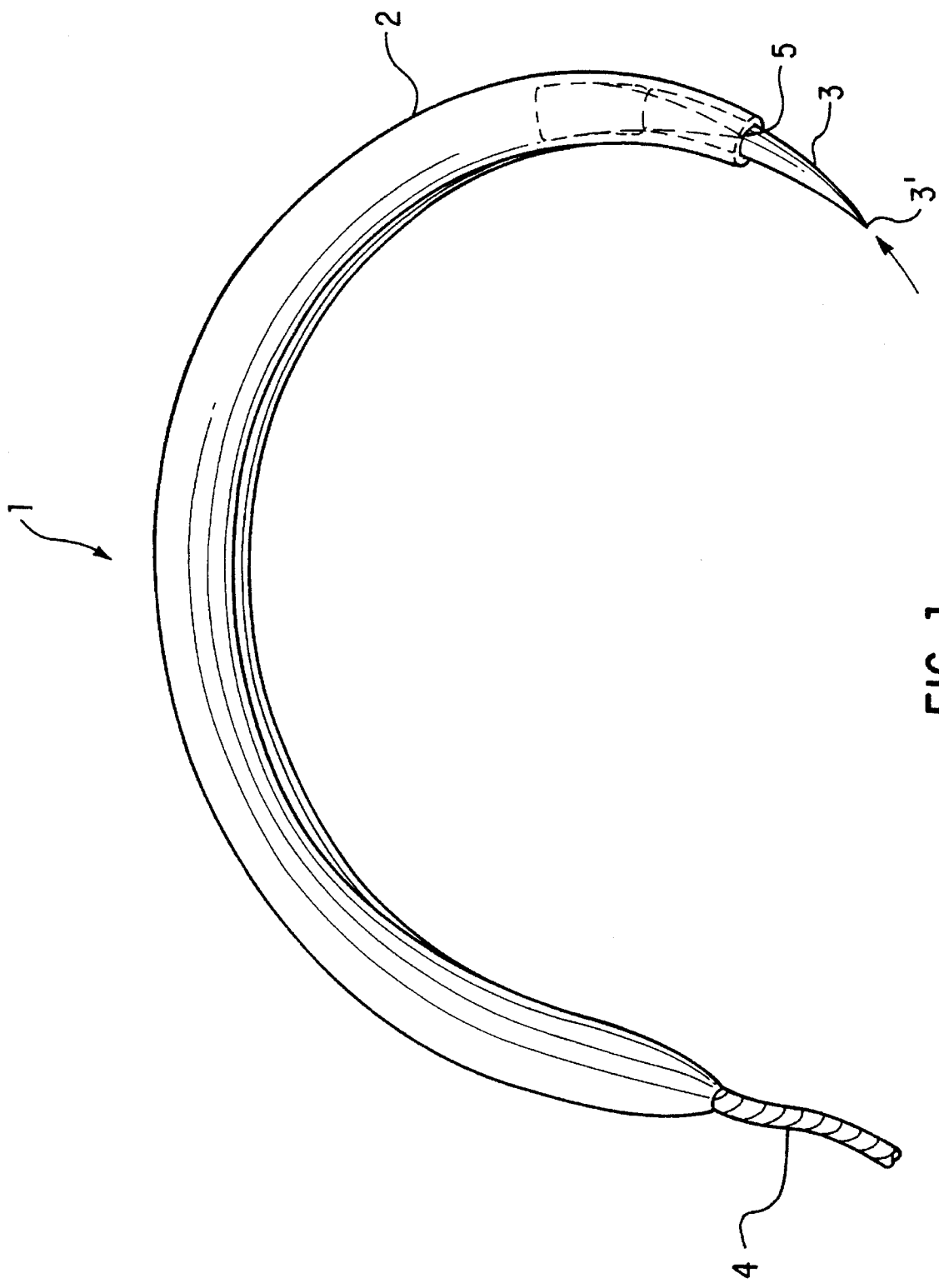
FIG. 1 is a side view of one embodiment of the invention.

FIG. 1 shows a surgical needle 1, with a suture 4 attached to one end of a hollow needle cover 2, and a needle 3 positioned inside of the hollow needle cover 2. When the needle 1 is locked into position for suturing use, the sharp tip 3' of the needle extends out of an opening 5 at the opposite end of the hollow needle cover 2. By striking the sharp tip 3' of the needle on a hard surface, the seal, which holds the needle 3 in place so that the sharp tip 3' extends through the opening 5 in the needle cover 2 and is exposed, is broken. The needle 3 collapses inside of the needle cover 2, thereby covering the sharp tip 3' and protecting the user from accidental needle-sticks.

Figure 2:
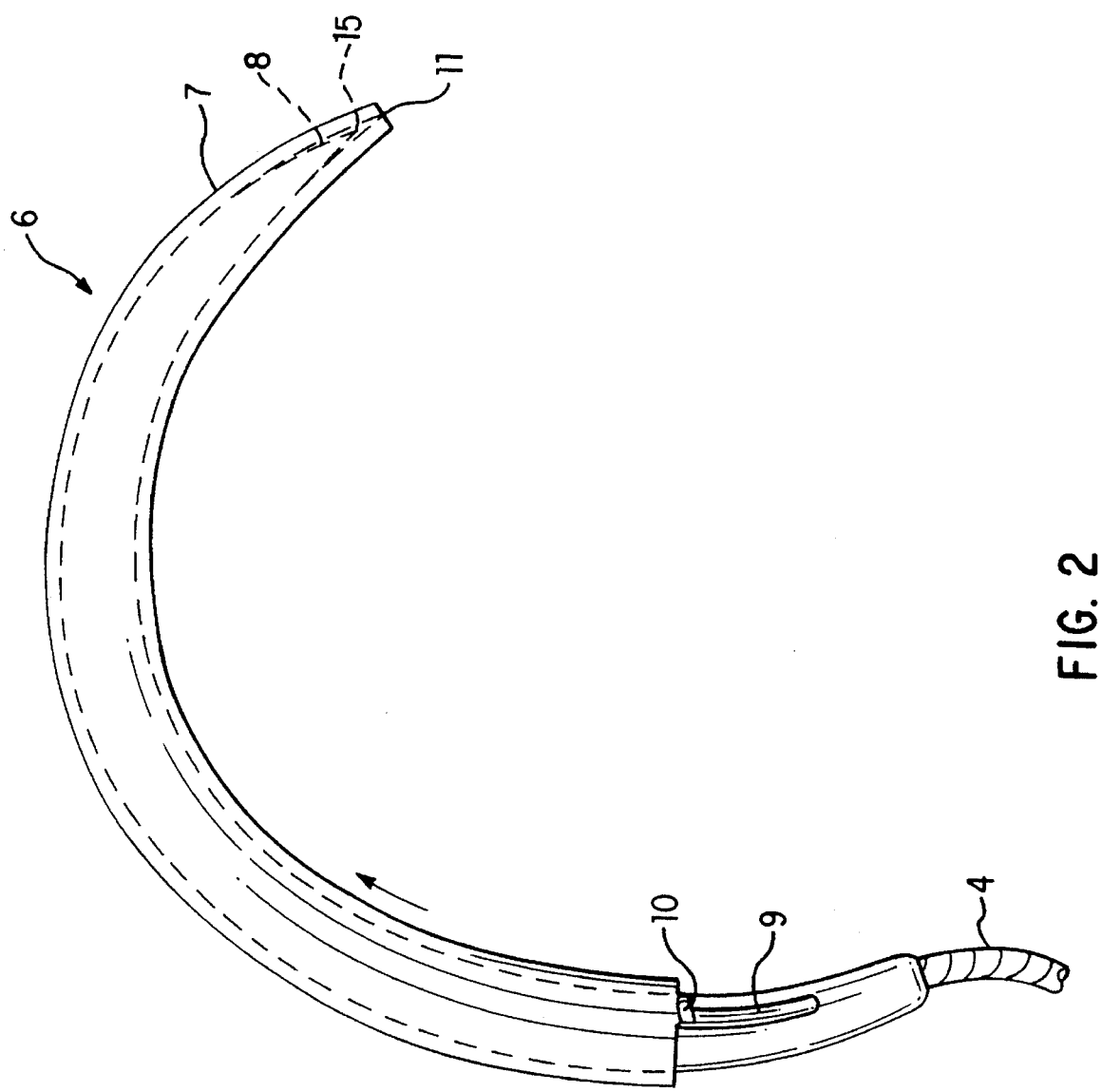
FIG. 2 is a side view of another embodiment of the invention.

FIG. 2 shows a surgical needle 6, with a suture 4 attached to one end of a needle 8. The needle 8 is positioned inside a hollow needle cover 7. The hollow needle cover 7 has an opening 11 at one end and is held in position by a lever mechanism 10 movably disposed within a groove 9 formed in the base of the needle 8. When the lever 10 is pushed so that it moves into the groove 9, the hollow needle cover slides back down the needle 8 so that the sharp point 15 of the needle 8 extends through the opening 11 in the hollow needle cover 7. When the hollow needle cover 7 slides forward along the needle 8 to the top of the groove 9, the lever 10 snaps out of the groove 9 to hold the hollow needle cover 7 in position, thereby covering the sharp point 15 of the needle 8, and protecting the user from accidental needle-sticks.

Figure 3:
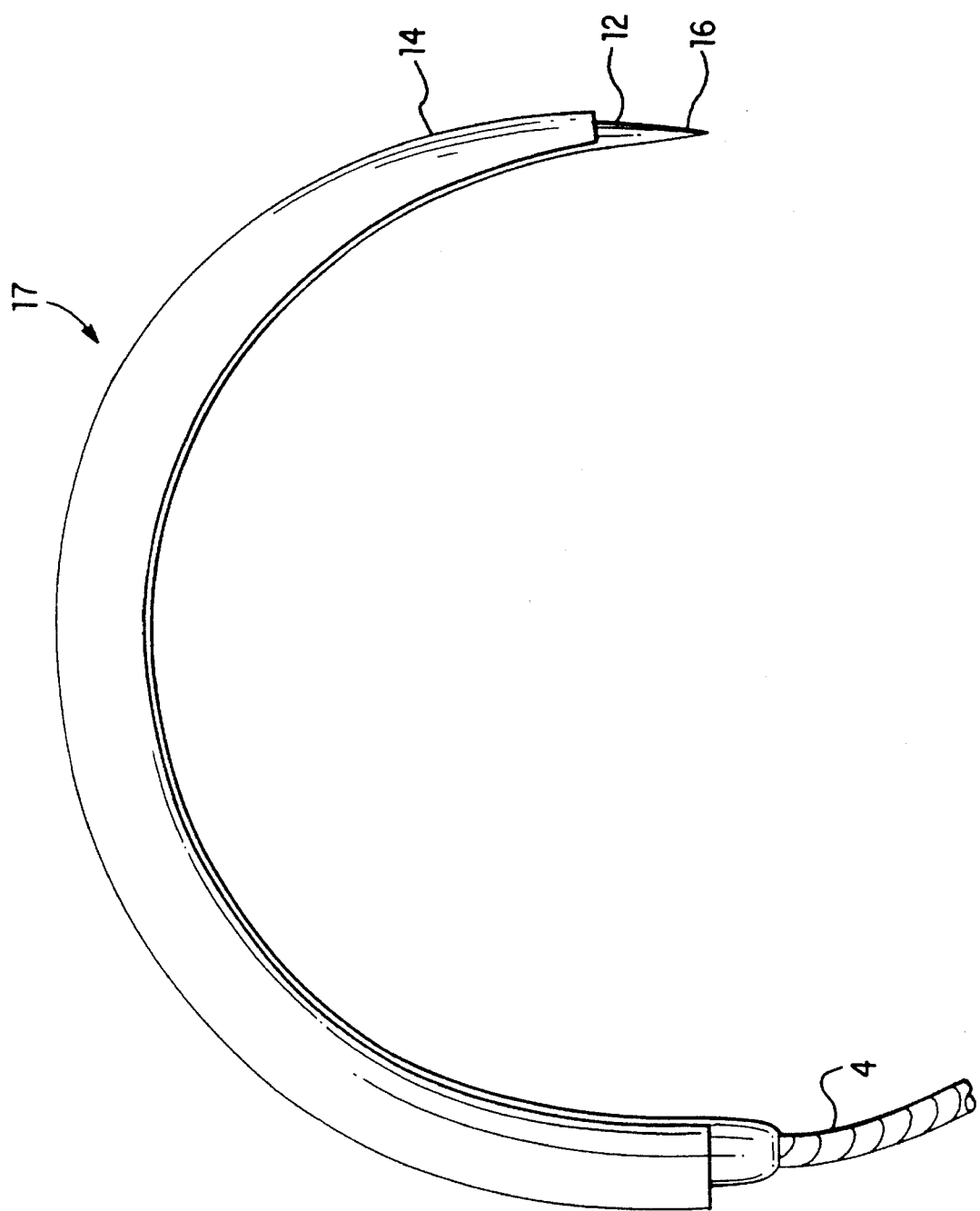
FIG. 3 is a side view of another embodiment of the invention.

FIG. 3 shows a surgical needle 17 with a suture 4 attached to one end of a needle 12. A hollow needle cover 14 is positioned around the needle 12 so that it partially covers the outer surface of the needle 12 and so that it slides forward and backward along the needle 12.

Figure 4:
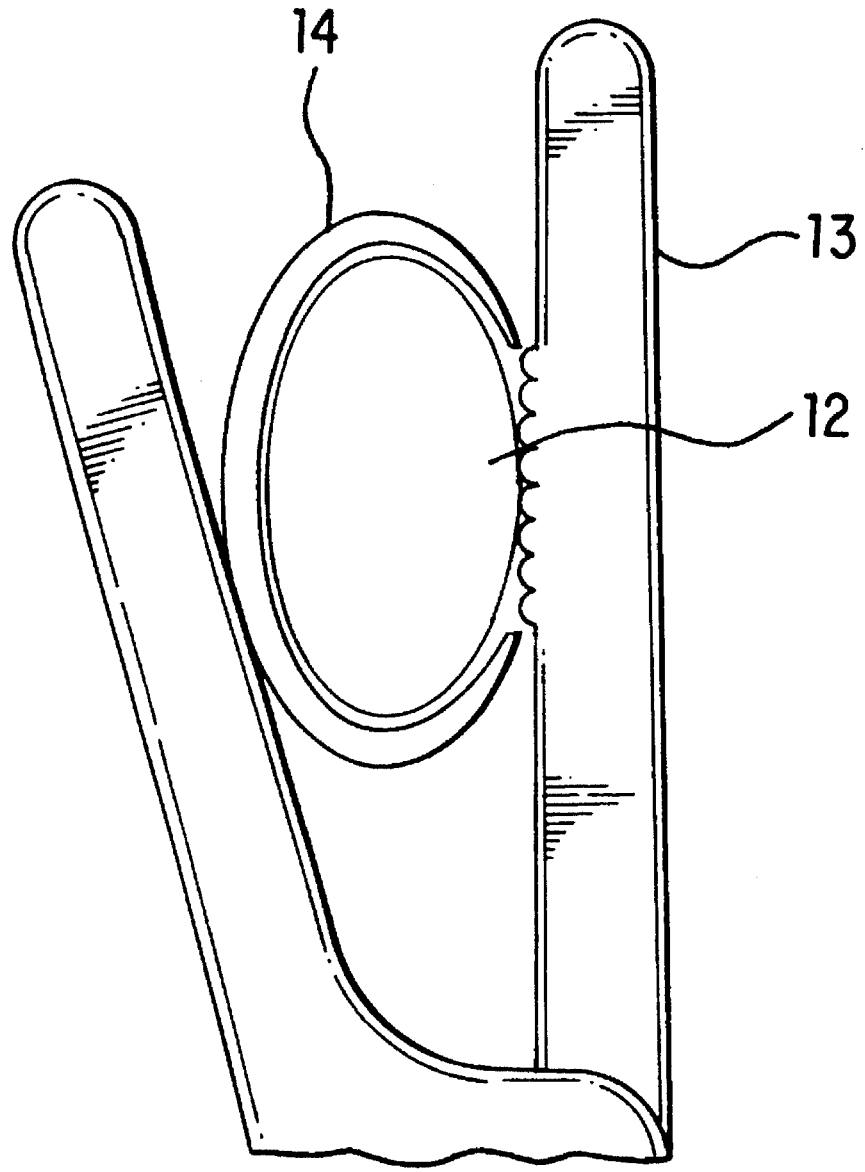
FIG. 4 is a side view showing a needle holder gripping the needle.

FIG. 4 shows when the surgical needle 17 is held in the needle holder 13, the needle holder contacts both the needle 12 and the hollow needle cover 14 and the needle cover 14 is prevented from sliding forward along the needle 17. When the surgical needle 17 is turned sideways in the needle holder 13, so that the needle holder 13 is only in contact with the hollow needle cover 14, the needle 12, when struck on a hard object, slides back into the hollow needle cover 14, thereby covering the sharp point of the needle and protecting the user against accidental needle-sticks.

What is claimed is:

1. A surgical needle, comprising:
    a needle having a suture attached to one end and a sharp tip formed at an opposite end;
    a hollow tubular needle cover extending the length of said needle and partially covering the outer surfaces of said needle having an opening at one end through which said sharp tip extends and a longitudinal slit formed therein in which said needle is slidably disposed, such that a portion of said needle is exposed along its length through said longitudinal slit for gripping by a needle holder, whereby when said needle and said cover are gripped by the needle holder, said sharp tip is exposed and when only said hollow needle cover is gripped by the needle holder and said sharp tip is struck on a hard surface, said needle cover slides forward to cover said sharp tip of said needle.

* * * * *